(12) United States Patent
Bouasaysy et al.

(10) Patent No.: US 9,358,143 B2
(45) Date of Patent: Jun. 7, 2016

(54) RETRIEVAL MECHANISMS FOR IMPLANTABLE MEDICAL DEVICES

(75) Inventors: Outhit Bouasaysy, Corona, CA (US); Mark Ashby, Laguna Niguel, CA (US)

(73) Assignee: ReShape Medical, Inc., San Clemente ( * ) Notice: Subject to any disclaimer, the term of this patent is extended or adjusted under 35 U.S.C. 154(b) by 871 days.

(21) Appl. No.: 13/386,647

(22) PCT Filed: Jul. 22, 2010

(86) PCT No.: PCT/US2010/042948
§ 371 (c)(1),
(2), (4) Date: Jul. 12, 2012

(87) PCT Pub. No.: WO2011/011629
PCT Pub. Date: Jan. 27, 2011

(65) Prior Publication Data
US 2012/0271338 A1    Oct. 25, 2012

Related U.S. Application Data

(60) Provisional application No. 61/227,764, filed on Jul. 22, 2009.

(51) Int. Cl.
*A61M 29/02* (2006.01)
*A61F 5/00* (2006.01)

(52) U.S. Cl.
CPC ............... *A61F 5/0036* (2013.01); *A61F 5/003* (2013.01)

(58) Field of Classification Search
CPC ..... A61F 5/003; A61F 5/0033; A61F 5/0036; A61F 5/0013; A61F 5/004; A61F 5/0043; A61F 5/0046; A61M 2025/1093
See application file for complete search history.

(56) References Cited

U.S. PATENT DOCUMENTS

| | | | |
|---|---|---|---|
| 1,166,690 A | * | 1/1916 | Kahn ................ A63H 27/10 206/522 |
| 2,493,326 A | | 1/1950 | Trinder |
| 4,133,315 A | | 1/1979 | Berman et al. |

(Continued)

FOREIGN PATENT DOCUMENTS

| DE | 8708978 U1 | 11/1987 |
|---|---|---|
| EP | 0103481 | 3/1984 |

(Continued)

OTHER PUBLICATIONS

Final Office Action; U.S. Appl. No. 11/694,536, Mailing Date Mar. 11, 2011, 13 pages.

(Continued)

*Primary Examiner* — Julian W Woo
*Assistant Examiner* — Shaun L David
(74) *Attorney, Agent, or Firm* — Perkins Coie LLP

(57) ABSTRACT

Improved devices and components for securing and retrieving an implantable medical device including at least one of a flanged tip disposed at a distal end of the implantable medical device; a halo retrieval tip disposed at a distal end of the implantable medical device; an external leash disposed at least one of a proximal end, a midportion, and a distal end of the implantable medical device; and an internal leash disposed within an inflatable balloon of the implantable medical device. A method of retrieving an implantable medical device, comprising: securing a retrieval device to at least one of the components described herein; and removing the implantable medical device from a patient.

9 Claims, 10 Drawing Sheets

(56) References Cited

U.S. PATENT DOCUMENTS

Figure 1:
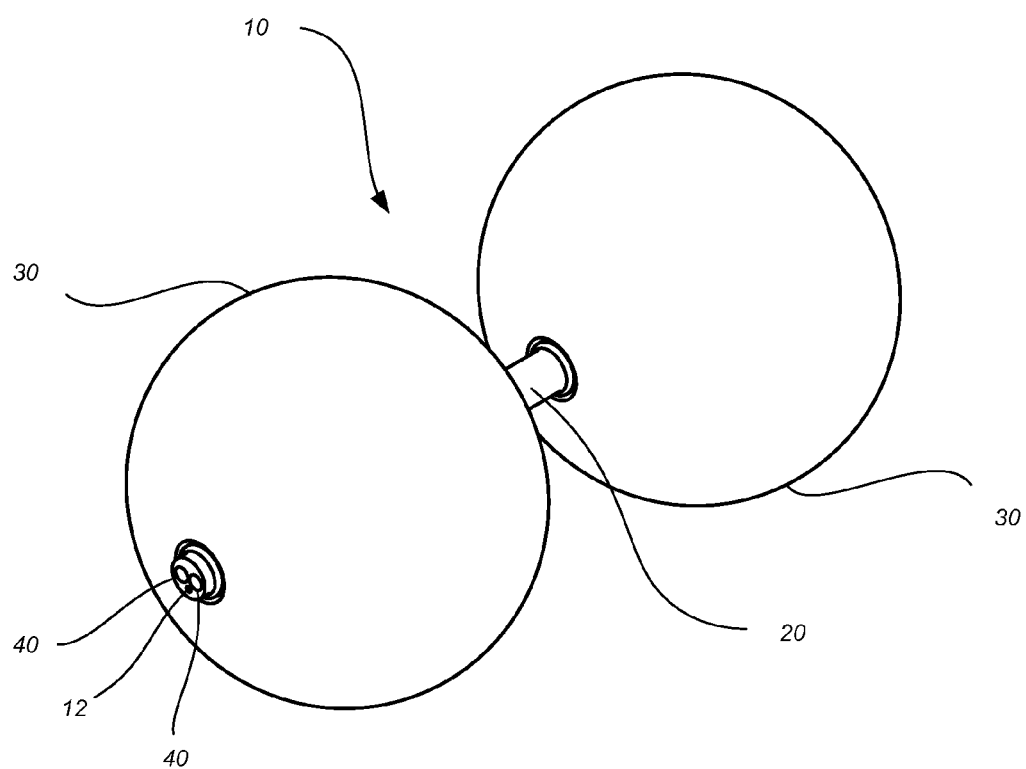

| Patent No. | | Date | Inventor |
|---|---|---|---|
| 4,198,983 | A | 4/1980 | Becker et al. |
| 4,246,893 | A | 1/1981 | Berson |
| 4,356,824 | A | 11/1982 | Vazquez |
| 4,368,739 | A | 1/1983 | Nelson, Jr. |
| 4,416,267 | A | 11/1983 | Garren et al. |
| 4,465,072 | A | 8/1984 | Taheri |
| 4,465,818 | A | 8/1984 | Shirahata et al. |
| 4,485,805 | A | 12/1984 | Foster, Jr. |
| 4,543,089 | A | 9/1985 | Moss |
| 4,598,699 | A | 7/1986 | Garren et al. |
| 4,694,827 | A | 9/1987 | Weiner et al. |
| 4,723,547 | A | 2/1988 | Kullas et al. |
| 4,899,747 | A | 2/1990 | Garren et al. |
| 4,940,458 | A | 7/1990 | Cohn |
| 5,073,347 | A | 12/1991 | Garren et al. |
| 5,084,061 | A * | 1/1992 | Gau ............... A61F 5/0036 604/103 |
| 5,123,840 | A | 6/1992 | Nates |
| 5,234,454 | A | 8/1993 | Bangs |
| 5,259,399 | A * | 11/1993 | Brown ............... A61F 5/004 128/897 |
| 5,263,934 | A | 11/1993 | Haak |
| 5,273,536 | A | 12/1993 | Savas |
| 5,318,530 | A | 6/1994 | Nelson, Jr. |
| 5,334,187 | A | 8/1994 | Fischell et al. |
| 5,431,173 | A | 7/1995 | Chin et al. |
| 5,496,271 | A | 3/1996 | Burton et al. |
| 5,516,812 | A | 5/1996 | Chu et al. |
| 5,575,772 | A | 11/1996 | Lennox |
| 5,639,810 | A | 6/1997 | Smith, III et al. |
| 5,643,209 | A | 7/1997 | Fugoso et al. |
| 5,730,722 | A | 3/1998 | Wilk |
| 5,779,728 | A | 7/1998 | Lunsford et al. |
| 5,857,991 | A | 1/1999 | Grothoff et al. |
| 5,876,376 | A | 3/1999 | Schwab et al. |
| 5,904,701 | A | 5/1999 | Daneshvar |
| 5,938,669 | A | 8/1999 | Klaiber et al. |
| 5,976,073 | A | 11/1999 | Ouchi |
| 5,993,473 | A * | 11/1999 | Chan ............... A61F 5/004 604/96.01 |
| 5,997,503 | A | 12/1999 | Willis et al. |
| 6,050,274 | A | 4/2000 | Gelardi et al. |
| 6,149,621 | A | 11/2000 | Makihara |
| 6,179,878 | B1 | 1/2001 | Duerig et al. |
| 6,254,355 | B1 | 7/2001 | Gharib |
| 6,276,567 | B1 | 8/2001 | Diaz et al. |
| 6,280,411 | B1 | 8/2001 | Lennox |
| 6,423,058 | B1 | 7/2002 | Edwards et al. |
| 6,427,089 | B1 | 7/2002 | Knowlton |
| 6,454,785 | B2 | 9/2002 | De Hoyos Garza |
| 6,524,234 | B2 | 2/2003 | Ouchi |
| 6,535,764 | B2 | 3/2003 | Imran et al. |
| 6,540,789 | B1 | 4/2003 | Silverman et al. |
| 6,547,788 | B1 | 4/2003 | Maguire et al. |
| 6,579,301 | B1 | 6/2003 | Bales et al. |
| 6,592,552 | B1 | 7/2003 | Schmidt |
| 6,613,018 | B2 | 9/2003 | Bagga et al. |
| 6,613,037 | B2 | 9/2003 | Khosravi et al. |
| 6,689,051 | B2 | 2/2004 | Nakada et al. |
| 6,706,010 | B1 | 3/2004 | Miki et al. |
| 6,746,460 | B2 | 6/2004 | Gannoe et al. |
| 6,826,428 | B1 | 11/2004 | Chen et al. |
| 6,850,128 | B2 | 2/2005 | Park |
| 6,866,657 | B2 | 3/2005 | Shchervinsky |
| 6,869,431 | B2 | 3/2005 | Maguire et al. |
| 6,890,300 | B2 | 5/2005 | Lloyd et al. |
| 6,890,346 | B2 | 5/2005 | Ganz et al. |
| 6,902,535 | B2 | 6/2005 | Eberhart et al. |
| 6,923,754 | B2 | 8/2005 | Lubock |
| 6,931,286 | B2 | 8/2005 | Sigg et al. |
| 6,939,299 | B1 | 9/2005 | Petersen et al. |
| 6,942,680 | B2 | 9/2005 | Grayzel et al. |
| 6,958,052 | B1 | 10/2005 | Charlton |
| 7,001,419 | B2 | 2/2006 | DiCaprio et al. |
| 7,016,735 | B2 | 3/2006 | Imran et al. |
| 7,020,531 | B1 | 3/2006 | Colliou et al. |
| 7,033,373 | B2 | 4/2006 | de la Torre et al. |
| 7,056,305 | B2 | 6/2006 | Garza Alvarez |
| 7,076,305 | B2 | 7/2006 | Imran et al. |
| 7,081,125 | B2 | 7/2006 | Edwards et al. |
| 7,131,945 | B2 | 11/2006 | Fink et al. |
| 7,483,746 | B2 | 1/2009 | Lee et al. |
| 7,625,355 | B2 | 12/2009 | Yu |
| 7,749,254 | B2 | 7/2010 | Sobelman et al. |
| 7,828,749 | B2 | 11/2010 | Douglas et al. |
| 7,931,693 | B2 | 4/2011 | Binmoeller et al. |
| 8,083,757 | B2 | 12/2011 | Gannoe et al. |
| 8,556,925 | B2 | 10/2013 | Makower et al. |
| 8,840,952 | B2 | 9/2014 | Ashby et al. |
| 8,894,568 | B2 | 11/2014 | Pecor et al. |
| 9,050,174 | B2 | 6/2015 | Pecor et al. |
| 9,149,611 | B2 | 10/2015 | Bouasaysy et al. |
| 2001/0022988 | A1 | 9/2001 | Schwarz et al. |
| 2001/0037127 | A1 | 11/2001 | De Hoyos Garza |
| 2002/0055757 | A1 | 5/2002 | Torre et al. |
| 2002/0107515 | A1 | 8/2002 | Edwards et al. |
| 2002/0161388 | A1 | 10/2002 | Samuels et al. |
| 2002/0173804 | A1 | 11/2002 | Rousseau |
| 2003/0105800 | A1 | 6/2003 | Cullen |
| 2003/0114878 | A1 | 6/2003 | Diederich et al. |
| 2003/0171768 | A1 | 9/2003 | McGhan |
| 2003/0187390 | A1 | 10/2003 | Bates et al. |
| 2004/0044354 | A1 | 3/2004 | Gannoe et al. |
| 2004/0059289 | A1 * | 3/2004 | Garza Alvarez . A61B 17/12099 604/96.01 |
| 2004/0059290 | A1 | 3/2004 | Palasis |
| 2004/0073162 | A1 | 4/2004 | Bleam et al. |
| 2004/0087902 | A1 | 5/2004 | Richter |
| 2004/0093058 | A1 | 5/2004 | Cottone et al. |
| 2004/0106899 | A1 | 6/2004 | McMichael et al. |
| 2004/0116897 | A1 | 6/2004 | Aboul-Hosn |
| 2004/0127915 | A1 | 7/2004 | Fleenor et al. |
| 2004/0186502 | A1 | 9/2004 | Sampson et al. |
| 2004/0220665 | A1 | 11/2004 | Hossainy et al. |
| 2004/0236280 | A1 | 11/2004 | Rice et al. |
| 2004/0236361 | A1 | 11/2004 | Sakurai |
| 2004/0254600 | A1 | 12/2004 | Zarbatany et al. |
| 2005/0027283 | A1 | 2/2005 | Richard et al. |
| 2005/0027313 | A1 | 2/2005 | Shaker |
| 2005/0038415 | A1 | 2/2005 | Rohr et al. |
| 2005/0055039 | A1 | 3/2005 | Burnett et al. |
| 2005/0059990 | A1 | 3/2005 | Ayala et al. |
| 2005/0075624 | A1 | 4/2005 | Miesel |
| 2005/0085792 | A1 | 4/2005 | Gershowitz |
| 2005/0119674 | A1 | 6/2005 | Gingras |
| 2005/0131442 | A1 | 6/2005 | Yachia et al. |
| 2005/0143784 | A1 | 6/2005 | Imran |
| 2005/0159769 | A1 | 7/2005 | Alverdy |
| 2005/0177103 | A1 | 8/2005 | Hunter et al. |
| 2005/0192615 | A1 | 9/2005 | Torre et al. |
| 2005/0267595 | A1 | 12/2005 | Chen et al. |
| 2005/0267596 | A1 | 12/2005 | Chen et al. |
| 2005/0273060 | A1 * | 12/2005 | Levy ............... A61B 17/1114 604/192 |
| 2006/0058829 | A1 | 3/2006 | Sampson et al. |
| 2006/0142700 | A1 * | 6/2006 | Sobelman ............... A61F 5/003 604/167.04 |
| 2006/0178691 | A1 | 8/2006 | Binmoeller |
| 2006/0184112 | A1 | 8/2006 | Horn et al. |
| 2006/0259020 | A1 | 11/2006 | Sharratt |
| 2007/0016262 | A1 | 1/2007 | Gross et al. |
| 2007/0078476 | A1 | 4/2007 | Hull et al. |
| 2007/0083224 | A1 | 4/2007 | Hively |
| 2007/0093728 | A1 | 4/2007 | Douglas et al. |
| 2007/0100367 | A1 | 5/2007 | Quijano et al. |
| 2007/0100368 | A1 | 5/2007 | Quijano et al. |
| 2007/0100369 | A1 | 5/2007 | Cragg et al. |
| 2007/0118168 | A1 * | 5/2007 | Lointier ............... A61F 5/003 606/192 |
| 2007/0135829 | A1 * | 6/2007 | Paganon ............... 606/192 |
| 2007/0142770 | A1 | 6/2007 | Rioux et al. |
| 2007/0149994 | A1 | 6/2007 | Sosnowski et al. |
| 2007/0173881 | A1 * | 7/2007 | Birk ............... A61F 5/003 606/192 |

(56) References Cited

U.S. PATENT DOCUMENTS

| | | |
|---|---|---|
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0085887 A1 | 4/2008 | Didiuk et al. |
| 2008/0097513 A1 | 4/2008 | Kaji et al. |
| 2008/0119729 A1 | 5/2008 | Copa et al. |
| 2008/0172079 A1* | 7/2008 | Birk ............... A61F 5/0036 606/192 |
| 2008/0190363 A1 | 8/2008 | Chen et al. |
| 2008/0208135 A1 | 8/2008 | Annunziata |
| 2008/0208241 A1 | 8/2008 | Weiner et al. |
| 2008/0233167 A1 | 9/2008 | Li et al. |
| 2008/0243071 A1 | 10/2008 | Quijano et al. |
| 2008/0243166 A1* | 10/2008 | Paganon ............ A61F 5/003 606/192 |
| 2008/0255601 A1 | 10/2008 | Birk |
| 2008/0312679 A1 | 12/2008 | Hardert et al. |
| 2008/0319471 A1 | 12/2008 | Sosnowski et al. |
| 2009/0048624 A1 | 2/2009 | Alverdy |
| 2009/0259236 A2 | 10/2009 | Burnett et al. |
| 2009/0275973 A1 | 11/2009 | Chen et al. |
| 2009/0287231 A1 | 11/2009 | Brooks et al. |
| 2010/0023047 A1 | 1/2010 | Simpson |
| 2010/0063530 A1* | 3/2010 | Valencon ............ A61F 5/003 606/192 |
| 2010/0130998 A1 | 5/2010 | Alverdy |
| 2010/0191270 A1* | 7/2010 | Garza Alvarez ...... A61F 5/0043 606/192 |
| 2010/0234853 A1 | 9/2010 | Pecor et al. |
| 2010/0243135 A1 | 9/2010 | Pepper et al. |
| 2010/0251837 A1 | 10/2010 | Bouasaysy et al. |
| 2010/0256667 A1* | 10/2010 | Ashby ............... A61F 5/0036 606/191 |
| 2011/0172767 A1 | 7/2011 | Rathi et al. |
| 2011/0178544 A1 | 7/2011 | Sosnowski et al. |
| 2011/0295300 A1* | 12/2011 | Verd ............... A61F 5/0036 606/192 |
| 2012/0191126 A1 | 7/2012 | Pecor et al. |
| 2012/0289992 A1 | 11/2012 | Quijano et al. |
| 2013/0035710 A1 | 2/2013 | Bouasaysy et al. |
| 2013/0053880 A1 | 2/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0031850 A1 | 1/2014 | Bouasaysy et al. |
| 2014/0257358 A1 | 9/2014 | Alverdy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor |

FOREIGN PATENT DOCUMENTS

| | | |
|---|---|---|
| EP | 0457456 A1 | 11/1991 |
| EP | 0485903 A2 | 5/1992 |
| EP | 1781183 | 5/2007 |
| FR | 2862525 A1 | 5/2005 |
| FR | 2892297 | 4/2007 |
| GB | 2090747 A | 7/1982 |
| GB | 2139902 A | 11/1984 |
| JP | S57168674 | 10/1982 |
| JP | 01015063 A | 1/1989 |
| JP | S6415063 | 1/1989 |
| JP | H091872 | 4/1989 |
| JP | H08322943 | 12/1996 |
| JP | 2001128985 | 5/2001 |
| JP | 20006333888 | 12/2006 |
| WO | 9000369 A1 | 1/1990 |
| WO | 9925418 A1 | 5/1999 |
| WO | WO-0141700 | 6/2001 |
| WO | WO-0166166 A2 | 9/2001 |
| WO | WO-0240081 | 5/2002 |
| WO | WO-2006035446 A2 | 4/2006 |
| WO | WO-2006056944 A1 | 6/2006 |
| WO | WO-2006/128978 A1 | 12/2006 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2007027812 | 4/2009 |
| WO | WO-2009055386 A2 | 4/2009 |
| WO | WO-2009112786 A2 | 9/2009 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011024077 A2 | 3/2011 |
| WO | WO-2011038270 A2 | 3/2011 |
| WO | WO-2011097637 A1 | 8/2011 |
| WO | WO-2011127205 A1 | 10/2011 |
| WO | WO2012048226 | 4/2012 |

OTHER PUBLICATIONS

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

International Search Report; International Application No. PCT/US2010/043136; Applicant: ReShape Medical, Inc., Mailing Date Apr. 12, 2011, 9 pages.

International Search Report; International Application No. PCT/US2010/050260; Applicant: ReShape Medical, Inc., Mailing Date: Jun. 17, 2011, 9 pages.

International Search Report; International Application No. PCT/US2011/026233; Applicant: ReShape Medical, Inc., Mailing Date Apr. 26, 2011, 9 pages.

International Search Report; International Application No. PCT/US2011/031463; Applicant: ReShape Medical, Inc., Mailing Date: Jun. 27, 2011, 10 pages.

International Search Report; International Application No. PCT/US2003/012782, Applicant: Applied Medical Resources Corporation, dated: Oct. 28, 2003, 7 pages.

International Search Report; International Application No. PCT/US2006/042336, Applicant: Abdominus, Inc., dated: Mar. 14, 2007, 9 pages.

International Search Report; International Application No. PCT/US2006/042710, Applicant: Abdominus, Inc. et al., dated: Mar. 15, 2007, 9 pages.

International Search Report; International Application No. PCT/US2006/042711, Applicant: Abdominus, Inc. et al, dated: Mar. 16, 2007, 9 pages.

International Search Report; International Application No. PCT/US2006/048647, Applicant: Abdominus, Inc. et al., dated: May 22, 2007, 12 pages.

International Search Report; International Application No. PCT/US2008/058677, Applicant: ReShape Medical et al., dated: Aug. 21, 2008, 12 pages.

International Search Report; International Application No. PCT/US2008/068058, Applicant: ReShape Medical, Inc. et al, dated: Nov. 19, 2008, 11 pages.

International Search Report; International Application No. PCT/US2010/029865, Applicant: ReShape Medical, Inc., dated: Jan. 5, 2011, 9 pages.

International Search Report; International Application No. PCT/US2011/024077; Applicant: ReShape Medical, Inc., dated: Apr. 6, 2011, 12 pages.

(56) References Cited

OTHER PUBLICATIONS

International Search Report; International Application No. PCT/US2011/024082, Applicant: ReShape Medical, Inc., dated: Apr. 6, 2011, 10 pages.
International Search Report; International Application No. PCT/US1155373, Applicant: Reshape Medical, Inc., dated: Jan. 20, 2012, 7 pages.
Living with the BIB: BioEnterics Intragastric Balloon Program: Patient Information; INAMED Health, dated 2004, 10 pages.
Non-Final Office Action; U.S. Appl. No. 11/694,536; dated: Oct. 26, 2011, 13 pages.
Non-Final Office Action; U.S. Appl. No. 12/625,473; dated Oct. 24, 2011, 18 pages.
ReShape Inflatable Gastric Ballon Going on Trial as Weight Loss Option, MedGadget: Internet Journal of Emerging Medical Technologies. Feb. 4, 2010, 5 pages.
Supplementary European Search Report for EP 03726447.0, mailed Mar. 1, 2006.
Wahlen CH et al. "The BioEnterics Intragastric Balloon: How to use it" Obesity Surgery 2001; 11:524-527.
Extended European Search Report; Application No. EP11766679.2, Applicant: Reshape Medical, Inc., mailed Dec. 12, 2013, 6 pages.
Extended European Search Report; Application No. EP11748141.6, Applicant: Reshape Medical, Inc., mailed Feb. 25, 2014, 6 pages.
Non-Final Office Action; U.S. Appl. No. 11/263,302; dated: Oct. 9, 2012, 6 pages.
Non-Final Office Action; U.S. Appl. No. 12/625,473; dated Jul. 12, 2012; 10 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
Extended European Search Report; Application No. EP6827098.3, Applicant: Reshape Medical, Corporation, mailed on Aug. 25, 2014, 3 pages.
Extended European Search Report; Application No. EP6827314.3, Applicant: ReShape Medical Corporation, mailed Aug. 1, 2014, 3 pages.
Extended European Search Report; Application No. EP6827313.5, Applicant: ReShape Medical Corporation, mailed Jul. 30, 2014, 5 pages.
Extended European Search Report; Application No. EP6847847.8, Applicant ReShape Medical Corporation, mailed Aug. 14, 2014, 5 pages.
Final Office Action; U.S. Appl. No. 13/858,767, mailed on May 30, 2014, 12 pages.
Non-Final Office Action; U.S. Appl. No. 13/386,638, mailed on Jun. 27, 2014, 12 pages.
Final Office Action; U.S. Appl. No. 13/858,767, Mailing Date May 22, 2103, 12 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,032, mailed on Jan. 28, 2014, 8 pages.
Non-Final Office Action; U.S. Appl. No. 13/386,650; mailed on Jun. 3, 2014, 15 pages.
Notice of Allowance; U.S. Appl. No. 12/753,803, dated May 13, 2014, 18 pages.
Ostrovsky, ReShape Inflatable Gastric Balloon going on Trial as Weight Loss Option; http://www.medgadget.com/2010/02/reshape_inflatable_gastric_balloon_system_going_on_trial_as_weight_loss_option.html Feb. 4, 2010, retrieved on Feb. 10-Feb. 13.
Non-Final Office Action; U.S. Appl. No. 12/723,545, date Feb. 29, 2012, 10 pages.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
Canadian Office Action; Application No. 2,691,530, mailed Dec. 18, 2014, 4 pages.
Canadian Office Action; Application No. CA 2638163, Applicant: ReShape Medical Corporation, mailed Mar. 10, 2015, 4 pages.
Canadian Office Action; Application No. CA 2638988, Applicant ReShape Medical Corporation, mailed Dec. 22, 2014 3 pages.
Canadian Office Action; Application No. CA 2638988, Applicant ReShape Medical Corporation, mailed Mar. 6, 2014, 4 pages.
Canadian Office Action; Application No. CA 2638989, Applicant: ReShape Medical Corporation, mailed May 22, 2013 3 pages.
Canadian Office Action; Application No. CA 2640554, Applicant: ReShape Medical Corporation, mailed May 27, 2013, 2 pages.
Canadian Office Action; Application No. CA2484838, Applicant: ReShape Medical, Inc., mailed Nov. 13, 2009, 3 pages.
Canadian Office Action; Application No. CA2484838, Applicant: ReShape Medical, Inc., mailed Sep. 24, 2010, 3 pages.
Canadian Office Action; Application No. CA2638163, Applicant: ReShape Medical Corporation, mailed Jul. 17, 2013, 2 pages.
Canadian Office Action; Application No. CA2638988, Applicant ReShape Medical Corporation, mailed Dec. 22, 2014 3 pages.
Canadian Office Action; Application No. CA2638988, Applicant: ReShape Medical Corporation, mailed May 28, 2013, 3 pages.
Canadian Office Action; Application No. CA2780085, Applicant: ReShape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. EP108002918.2, Applicant: ReShape Medical Inc., mailed Dec. 17, 2014, 5 pages.
European Examination Report; Application No. EP108029943, Applicant: ReShape Medical Inc., mailed Dec. 18, 2014, 4 pages.
European Examination Report; Application No. 08771842.5, May 7, 2015, 5 pages.
European Supplementary Search Report; Application No. 08771842.5, Apr. 24, 2015, 3 pages.
Extended European Search Report; Application No. 08732989.2, Applicant: ReShape Medical, Inc., mailed Oct. 16, 2014, 7 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application No. JP2013-43712, mailed Jan. 8, 2015, 8 pages.
Japanese Office Action; Application. No. JP2013-043712, mailed Apr. 22, 2013, 5 pages.
Canadian 2nd Office Action Application No. CA 2680124, Applicant: ReShape Medical, Inc., mailed Jul. 9, 2015, 3 pages.
European Examination Report; Application No. EP06827313.5, Applicant: ReShape Medical Inc., mailed Jul. 13, 2015, 4 pages.
European Examination Report; Application No. EP06847847.8, Applicant: ReShape Medical Inc., mailed Jul. 13, 2015, 4 pages.
Japanese Office Action; Application No. 2013-532976; mailed Jun. 26, 2015, 10 pages.
Cronin et al., "Normal small bowel wall characteristics on MR enterography," European Journal of Radiology 74 (2)207-211, Aug. 2010.
Gray, Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Canadian Office Action, Application No. CA 2638163, Applicant: Reshape Medical, Inc., mailed Dec. 8, 2015, 4 pages.

(56) References Cited

OTHER PUBLICATIONS

Final Office Action for Japanese Application No. 2014-52972, Applicant: ReShape Medical, Inc., mailed on Oct. 9, 2015, 8 pages.

Partial Supplementary European Search Report for European Application No. 11740535.7, Applicant: ReShape Medical, Inc., mailed Oct. 20, 2015, 7 pages.

* cited by examiner

RETRIEVAL MECHANISMS FOR IMPLANTABLE MEDICAL DEVICES

RELATED APPLICATION

The present application is a U.S. National Phase application under 35 U.S.C. 371 of International Application Serial No. PCT/US2010/042948, filed Jul. 22, 2010, which claims the benefit of U.S. Provisional Patent Application Ser. No. 61/227,764, filed Jul. 22, 2009, the entire contents of which are incorporated herein by reference in their entireties.

This application incorporates by reference U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; WIPO Pub. No. WO/2008/121831, published Oct. 9, 2008; WIPO Pub. No. WO/2009/002989, published Dec. 31, 2008; each as if fully set forth herein in its entirety.

BACKGROUND

This disclosure relates to deflation and retrieval mechanisms, process, and systems for implantable medical devices. In particular, this disclosure relates to deflation and retrieval of intragastric devices.

SUMMARY

According to embodiments, disclosed is an implantable gastric device, comprising: a shaft having a distal end and a proximal end; a balloon coupled to the shaft; a flanged tip disposed at the distal end of the shaft, the flanged tip comprising a body and a plurality of flanges extending radially outward from the body, the flanges forming an interrupted and atraumatic surface at a distal end of the flanged tip.

The shaft may further comprise a lumen extending axially within the shaft from the proximal end to the distal end and fluidly connected to an interior of the balloon. The flanged tip may further comprise a plug configured to seal the lumen at the distal end when the flanged tip is coupled to the shaft.

The shaft may further comprise a guidewire channel extending axially within the shaft from the proximal end to the distal end. The flanged tip may further comprise a guidewire hole configured to be aligned with the guidewire channel of the shaft when the flanged tip is coupled to the shaft.

A recess may be defined between the flanges, the body, and the balloon, wherein the recess provides a location for securing a retrieval device.

The flanges may define a head at a distal end of the flanged tip, the head providing a substantially smooth, convex surface. The convex surface may shaped such that imaginary extensions of the convex surface extending from the flanges as viewed in profile are aligned to tangentially graze the surface of the balloon while in an inflated state. The convex surface has a profile of a spherical cap formed by a sphere cut off by a plane other than at the center of the sphere. The body may substantially cylindrical. The radius of the spherical cap may larger than the radius of the body.

According to embodiments, disclosed is an implantable gastric device, comprising: a shaft having a distal end and a proximal end; a balloon coupled to the shaft; a halo tip disposed at the distal end of the shaft, wherein the halo tip comprises a body and a ring connected to the body by a bridge, wherein a recess between the ring and the body is provided for securing a retrieval device to the halo tip. The ring may within a plane orthogonal to an axis of the shaft.

The ring of the halo tip comprises a central opening provided for securing a retrieval device to the halo tip.

The shaft may further comprise a lumen extending axially within the shaft from the proximal end to the distal end and fluidly connected to an interior of the balloon. The halo tip may further comprise a plug configured to seal the lumen at the distal end when the halo tip is coupled to the shaft.

The shaft may further comprise a guidewire channel extending axially within the shaft from the proximal end to the distal end. The halo tip may further comprise a guidewire hole configured to be aligned with the guidewire channel of the shaft when the halo tip is coupled to the shaft.

According to embodiments, disclosed is an implantable gastric device, comprising: a shaft having a distal end and a proximal end; a balloon coupled to the shaft; a leash coupled to the shaft, wherein the leash is configured to extend from the shaft and provide an attachment location for a retrieval device.

The leash may disposed at one of the proximal end of the shaft, the distal end of the shaft, and a medial portion between the proximal end and the distal end of the shaft. The leash may disposed within the balloon. The leash may configured to retract when under a load from a surrounding environment and extend radially outward from the shaft when in a natural state.

The leash may at least one of a hoop, a ring, a hook, a clasp, a fastener, a pin, a clip, a flange, a strap, an articulated joint, and a curved portion.

The shaft may be of a material having between about 50 A durometer and about 60 A durometer.

According to embodiments, disclosed is a method of retrieving an implantable medical device, comprising: securing a retrieval device to at least one of a flanged tip disposed at a distal end of the implantable medical device; a halo retrieval tip disposed at a distal end of the implantable medical device; a leash disposed at least one of a proximal end, a midportion, and a distal end of the implantable medical device; and a leash disposed within an inflatable balloon of the implantable medical device; and removing the implantable medical device from a patient.

According to embodiments, disclosed is an implantable medical device, comprising: at least one inflatable balloon; and a shaft extending through the at least one balloon, wherein the shaft is of a material having about 55 A durometer, and wherein the shaft provides improved trackability and reduces trauma to the implant location.

DRAWINGS

Figure 2A:
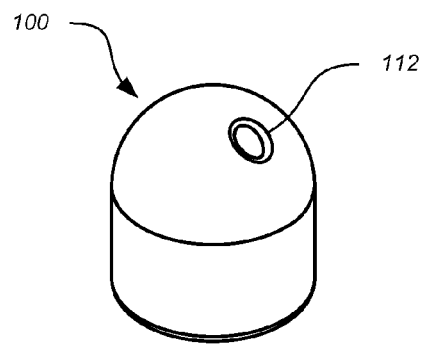
Figure 2B:
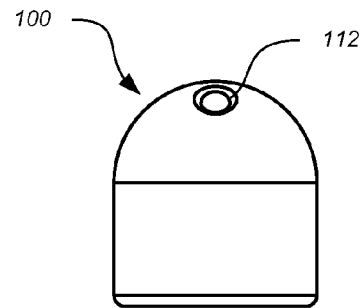
Figure 2C:
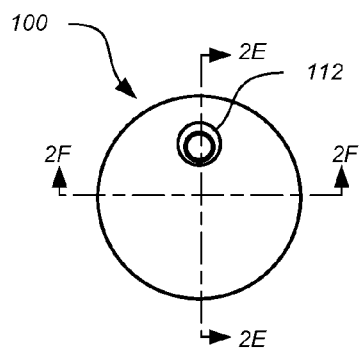
Figure 2D:
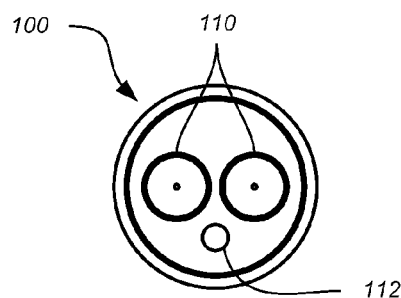
Figure 2E:
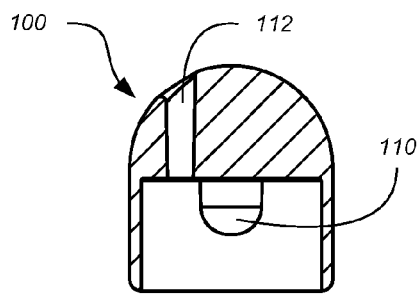
Figure 2F:
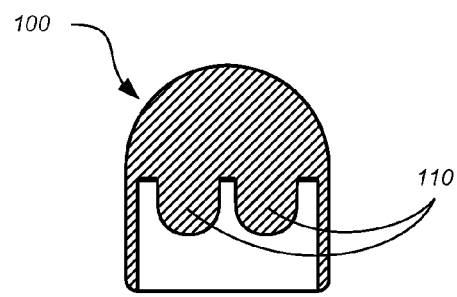
Figure 3:
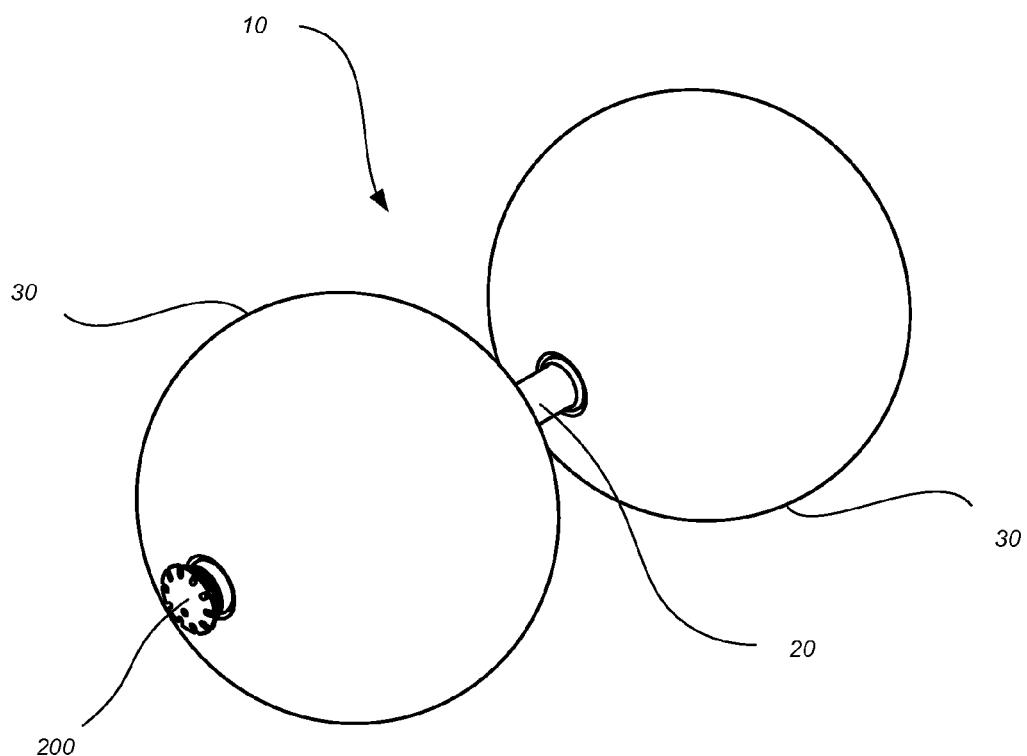
Figure 4A:
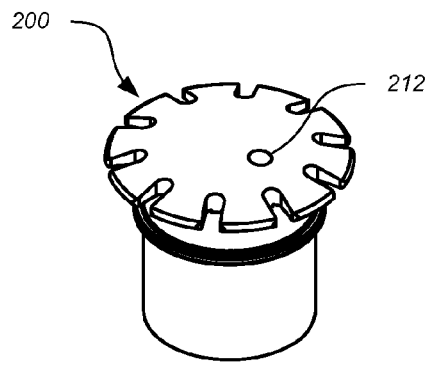
Figure 4B:
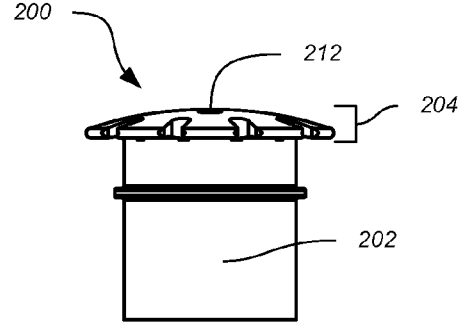
Figure 4C:
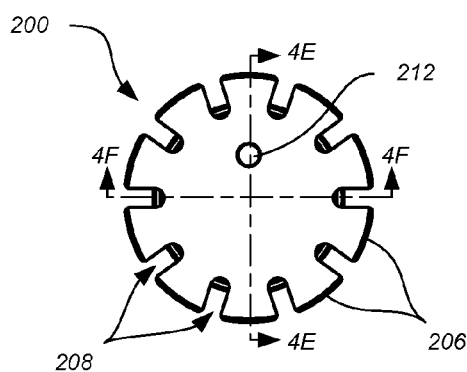
Figure 4D:
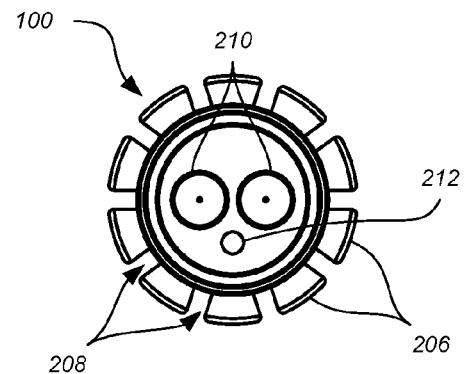
Figure 4E:
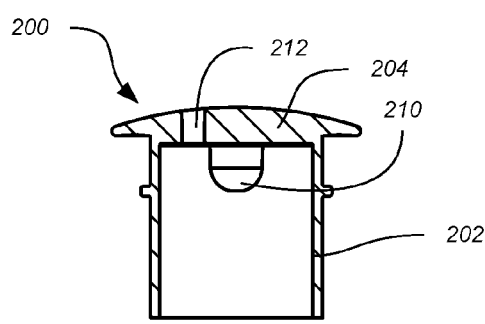
Figure 4F:
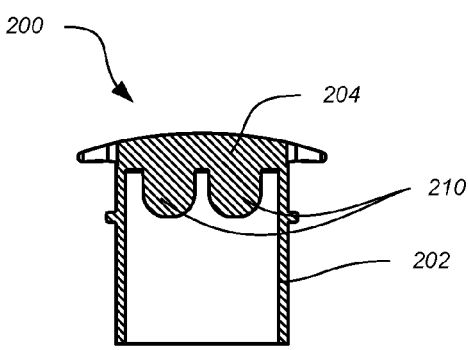
Figure 5:
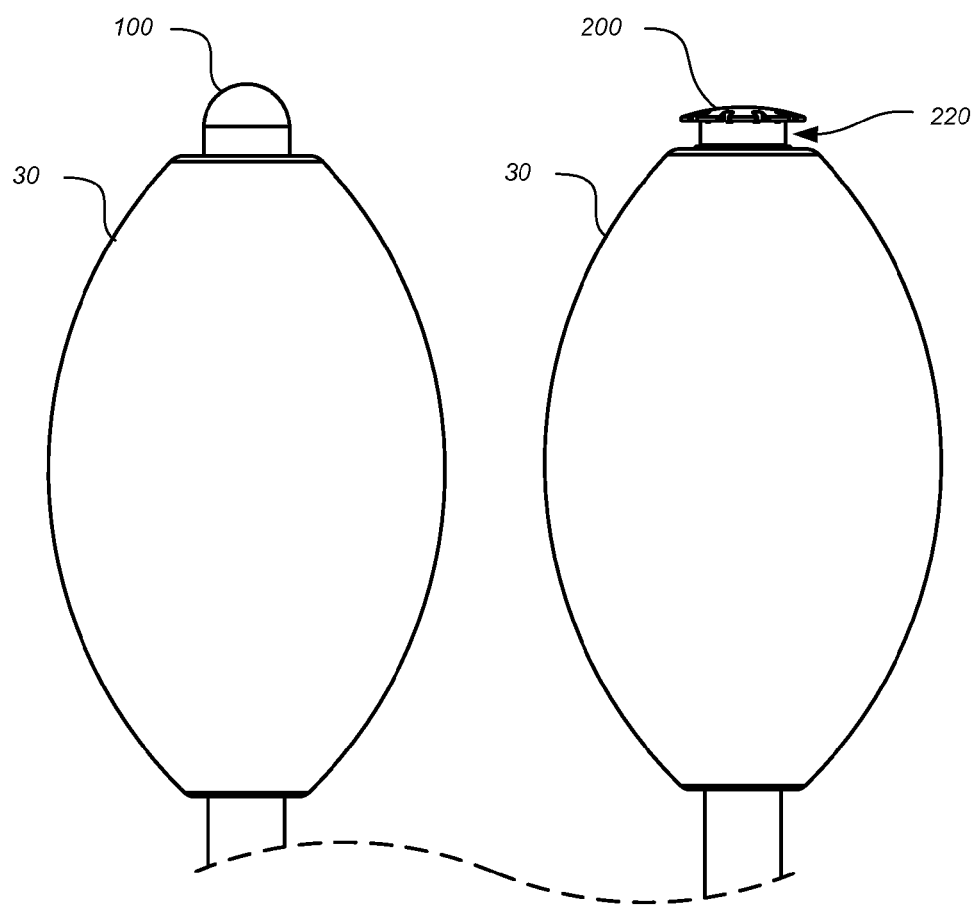
Figure 6A:
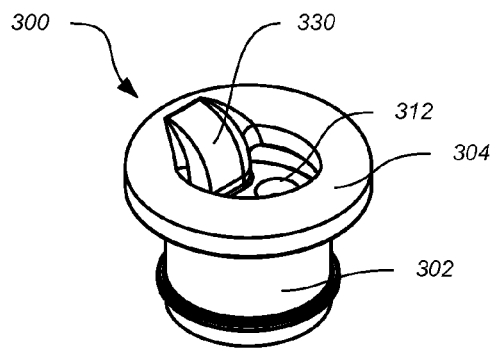
Figure 6B:
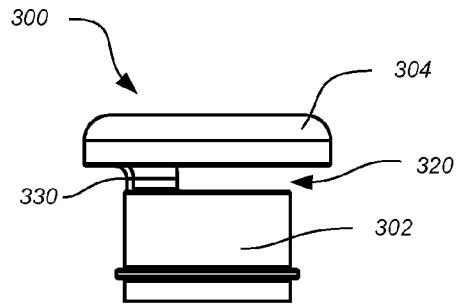
Figure 6C:
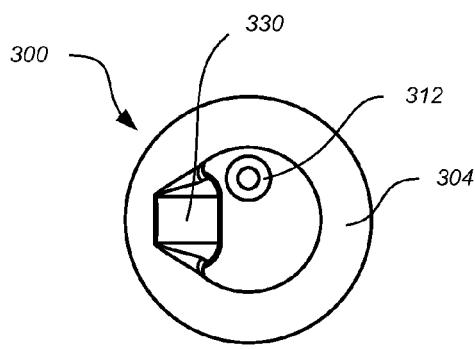
Figure 6D:
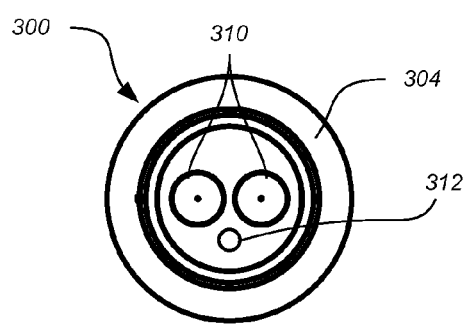
Figure 6E:
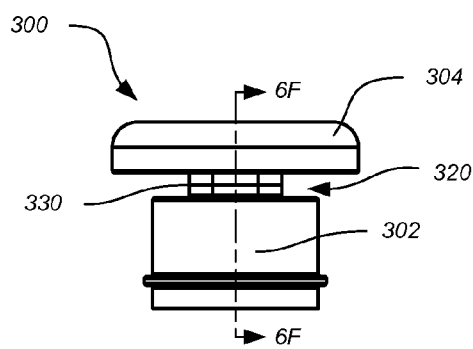
Figure 6F:
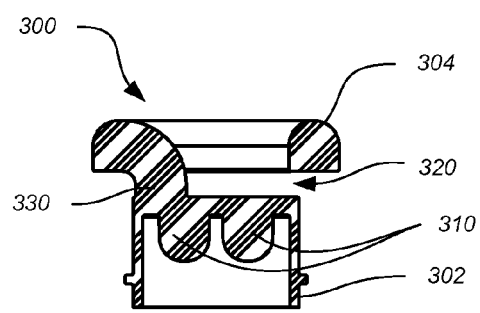
Figure 7:
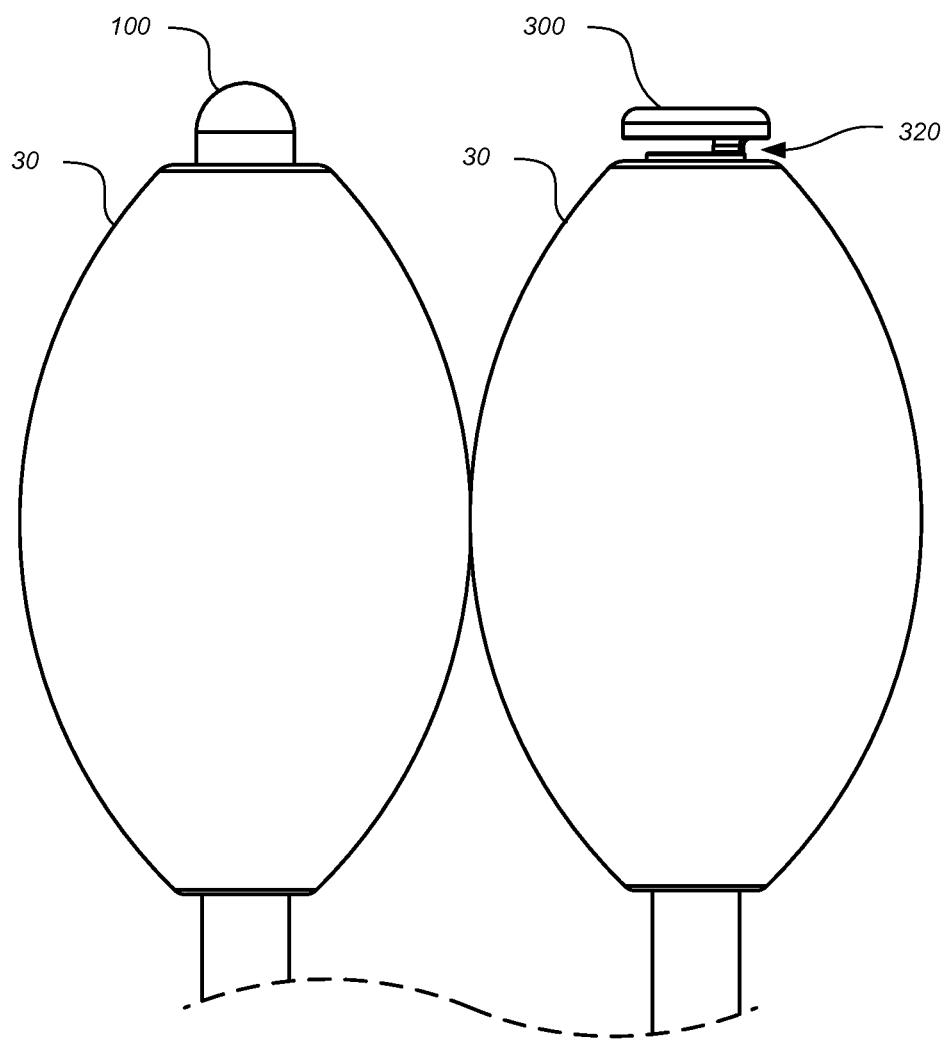
Figure 8:
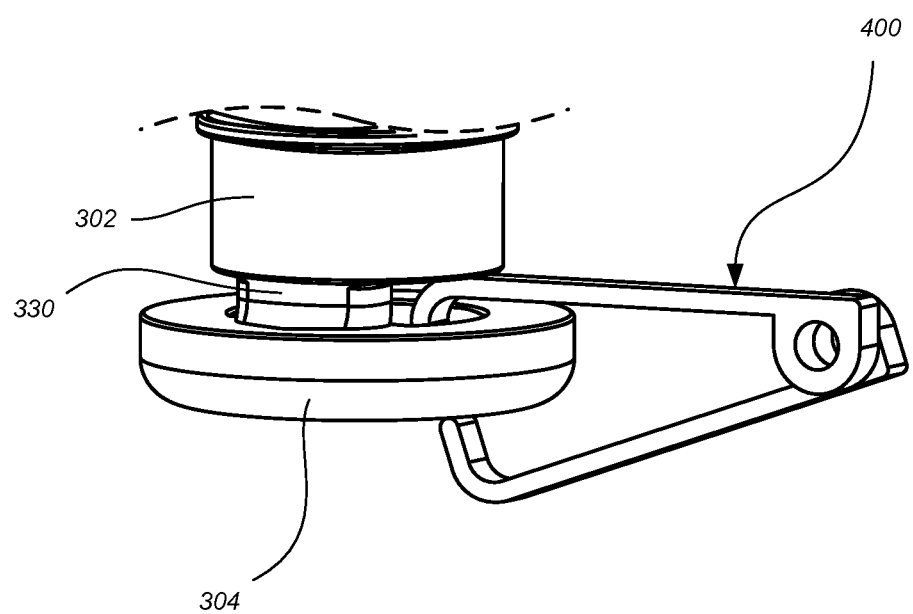
Figure 9:
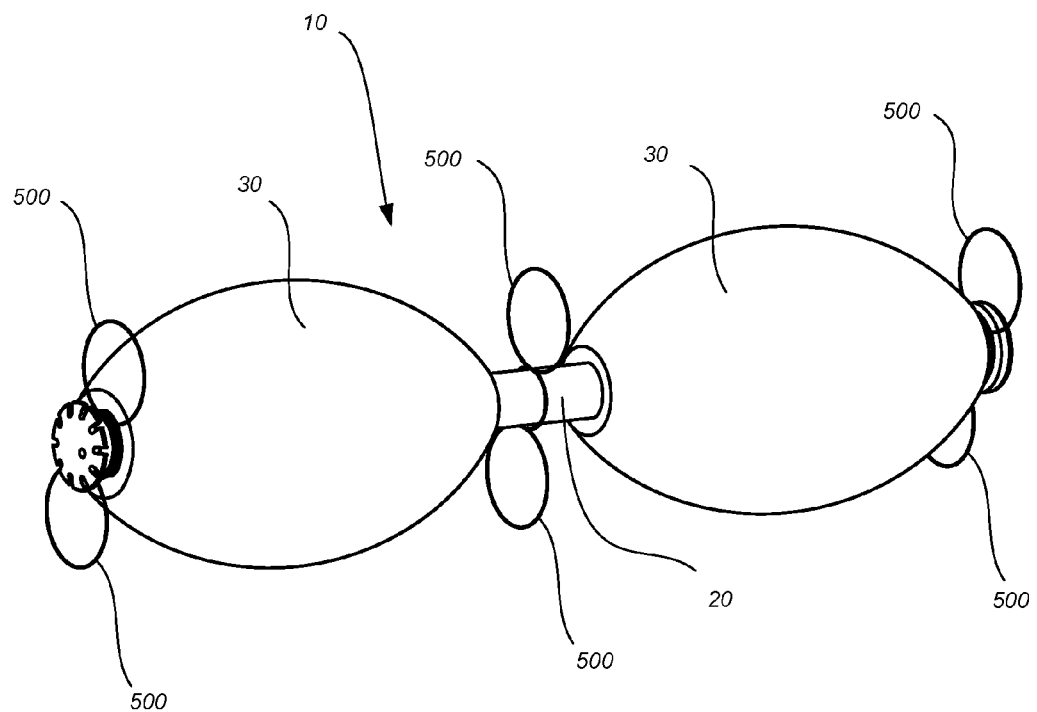
Figure 10:
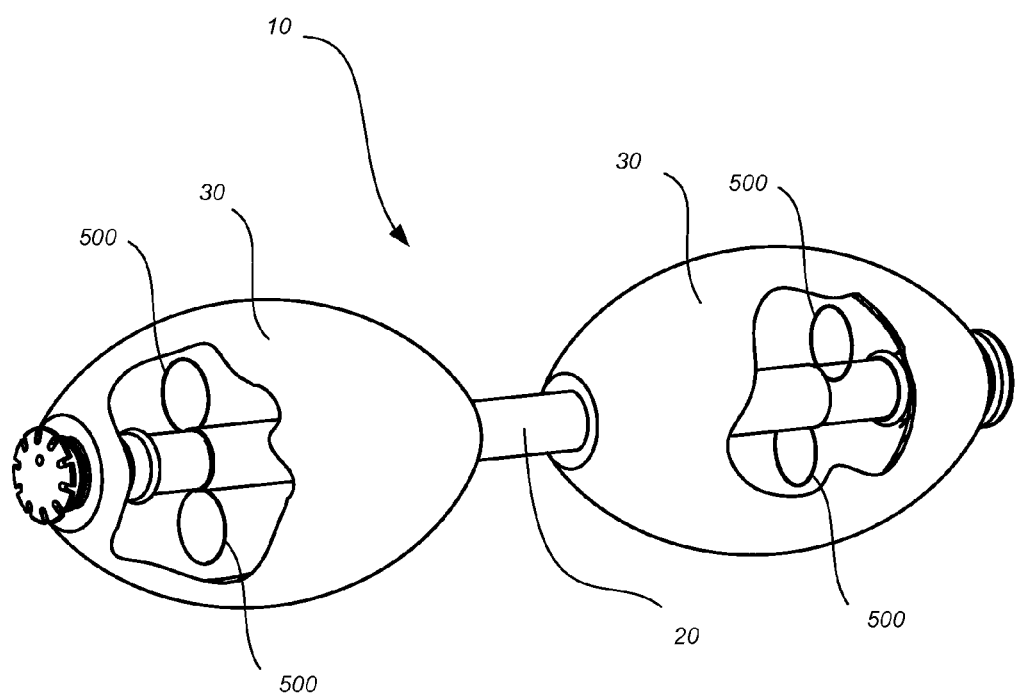

The above-mentioned features and objects of the present disclosure will become more apparent with reference to the following description taken in conjunction with the accompanying drawings wherein like reference numerals denote like elements and in which:

FIG. 1 shows a perspective view of an intragastric device;
FIG. 2A shows a perspective view of a rounded tip;
FIG. 2B shows a side view of a rounded tip;
FIG. 2C shows a top view of a rounded tip;
FIG. 2D shows a bottom view of a rounded tip;
FIG. 2E shows a sectional view of a rounded tip;
FIG. 2F shows a sectional view of a rounded tip;
FIG. 3 shows a perspective view of an intragastric device with flanged tip;

FIG. 4A shows a perspective view of a flanged tip;
FIG. 4B shows a side view of a flanged tip;
FIG. 4C shows a top view of a flanged tip;
FIG. 4D shows a bottom view of a flanged tip;
FIG. 4E shows a sectional view of a flanged tip;
FIG. 4F shows a sectional view of a flanged tip;
FIG. 5 shows a view of a rounded tip (left) and a flanged tip (right);
FIG. 6A shows a perspective view of a halo tip;
FIG. 6B shows a side view of a halo tip;
FIG. 6C shows a top view of a halo tip;
FIG. 6D shows a bottom view of a halo tip;
FIG. 6E shows a front view of a halo tip;
FIG. 6F shows a sectional view of a halo tip;
FIG. 7 shows a view of a rounded tip (left) and a halo tip (right);
FIG. 8 shows a view of a halo tip and a grasper;
FIG. 9 shows a perspective view of an intragastric device having external leashes; and
FIG. 10 shows a broken-out partial sectional of an intragastric device having internal leashes.

DETAILED DESCRIPTION

According to embodiments, intragastric device 10 is provided as disclosed herein. Intragastric device 10 includes at least one expandable, space-filling component, such as balloon 30. As shown in FIG. 1, a plurality of balloons 30 (e.g., proximal and distal) may be coupled to shaft 20 of intragastric device 10.

According to embodiments, and as shown in FIG. 1, shaft 20 of intragastric device 10 is configured to interface with a tip at a proximal or distal end thereof. As used herein, the terms "proximal" and "distal" refer to relative locations and orientations of structures, devices, and components. For example, the terms "proximal" and "distal" may be understood to refer to relative identifiers, rather than absolute identifiers except where expressly stated as such. As those having skill in the relevant art will recognize, variation and modification of the disclosure on the same basis is considered within the present disclosure.

According to embodiments, and as shown in FIG. 1, shaft 20 of intragastric device 10 includes a plurality of lumens 40, each corresponding to a balloon 30 of intragastric device 10 for inflation or deflation thereof. For example, each lumen 40 may be continually, variably, controllably, or selectably in fluid communication with an interior portion of one of balloons 30. Each lumen 40 may extend axially within shaft 20.

According to embodiments, and as shown in FIG. 1, guidewire channel 12 extends axially within shaft 20 of intragastric device 10. Guidewire channel 12 may be configured to accommodate a guidewire for assisted delivery and management of intragastric device 10 during implant, explant, or maintenance thereof.

According to embodiments, intragastric device 10 has a variety of applications and uses. According to embodiments, intragastric device 10 is an implant that may be configured for temporary use and explanted after some period of time. The explant procedure may utilize tools including, but not limited to, an endoscope and a snare, forceps, or other gripping or capturing tools. The endoscope may have a single working channel and may be positioned parallel to the gastric device and in a retro-flexed manner (U-turn) for visualization and access to a distal end. Part of the challenge of explanting is the lack of explant friendly features on a device having atraumatic design and overall smooth profile. In general, solutions that both improve the explant portion of the procedure as well as maintain or improve the overall atraumatic nature of the device with a smooth profile are desirable.

According to embodiments, as shown in FIGS. 2A, 2B, 2C, 2D, 2E, and 2F, rounded tip 100 may be provided for an end of intragastric device 10. Rounded tip 100 may be coupled to an end of intragastric device 10 at shaft 20. For example, plugs 110 of rounded tip 100 may be aligned relative to lumens 40 of shaft 20, whereby plugs 110 seal lumens 40 at ends thereof. Further, guidewire hole 112 of rounded tip 100 may be aligned relative to guidewire channel 12 of shaft 20.

According to embodiments, as shown in FIGS. 2A, 2B, 2C, 2D, 2E, and 2F, rounded tip 100 may have a cylindrical portion and a generally hemispherical end. The radius of the cylindrical portion may be substantially equal to the radius of the generally hemispherical end.

At least a portion of each plug 110 is configured to seal at least a portion of a corresponding lumen 40 when rounded tip 100 is coupled to shaft 20. Accordingly, plugs 110 may be of a rigid, semi-rigid, or flexible material to facilitate such sealing. The geometry of the plugs 110 may correspond to that of the lumens 40. For example, plugs 110 may have similar cross-sectional geometry as that of the lumens 40, to provide proper sealing. The size, diameter, etc. of plugs 110 may exceed that of lumens 40 by a margin sufficient to facilitate sealing against pressure from within lumens 40. For example, radial pressure provided outwardly from plug 110 against walls of lumen 40 into which it is inserted may provide frictional forces, electrostatic forces, Van der Waals forces, or hydrogen bonding forces, inter alia, to resist pressure from within lumen 40 tending to push plug 110 out of lumen 40.

The periphery of rounded tip 100 provides a smooth profile for reducing trauma to surrounding environment when placed in situ. However, the cylindrical sides and generally hemispherical end make rounded tip 100 difficult to engage. Once engaged, its smooth sides allow it to slip through the retrieval device (such as a snare). The user can possibly lose the device in an area, potentially causing patient distress and prolonging an explant procedure.

According to embodiments of the present disclosure, improved retrieval mechanisms and methods have been developed that both achieve atraumatic design functionality and facilitate explant, retrieval, and removal of intragastric device 10.

According to embodiments, and as shown in FIG. 3, flanged tip 200 may be provided to selectably seal the distal end of intragastric device 10. According to embodiments, as shown in FIGS. 4A, 4B, 4C, 4D, 4E, and 4F, flanged tip 200 may be provided for an end of intragastric device 10. Flanged tip 200 may be coupled to an end of intragastric device 10 at shaft 20. For example, plugs 210 of flanged tip 200 may be aligned relative to lumens 40 of shaft 20, whereby plugs 210 seal lumens 40 at ends thereof. Further, guidewire hole 212 of flanged tip 200 may be aligned relative to guidewire channel 12 of shaft 20.

At least a portion of each plug 210 is configured to seal at least a portion of a corresponding lumen 40 when flanged tip 200 is coupled to shaft 20. Accordingly, plugs 210 may be of a rigid, semi-rigid, or flexible material to facilitate such sealing. The geometry of the plugs 210 may correspond to that of the lumens 40. For example, plugs 210 may have similar cross-sectional geometry as that of the lumens 40, to provide proper sealing. The size, diameter, etc. of plugs 210 may exceed that of lumens 40 by a margin sufficient to facilitate sealing against pressure from within lumens 40. For example, radial pressure provided outwardly from plug 210 against walls of lumen 40 into which it is inserted may provide frictional forces, electrostatic forces, Van der Waals forces, or hydrogen bonding forces, inter alia, to resist pressure from within lumen 40 tending to push plug 210 out of lumen 40.

According to embodiments, and as shown in FIGS. 4A, 4B, 4C, 4D, 4E, and 4F, Flanged tip 200 may include body 202 and head 204. According to embodiments, flanges 206 extend radially outward from portions of head 204. Flanges 206 may extend radially beyond circumferential limit of at least one other components, such as body 202. Flanges 206 provide increased surface area across head 204, whereby forces applied at head 204 are distributed across a greater surface area. This reduces or eliminates tendencies to induce trauma.

Flanges 206 may be provided in a variety of geometries. For example, as shown in FIG. 4B, head 204 and flanges 206 may form a substantially smooth, convex surface in profile, which may be viewed as a curved arc. Head 204 and flanges 206 may be configured such that imaginary extensions of such a curved arc may aligned to tangentially graze the surface of nearby balloons 30 (as shown in FIG. 5). In other words, in at least some embodiments, the convex surface is shaped such that imaginary extensions of the convex surface extending from flanges 206 as viewed in profile are aligned to tangentially graze the surface of balloon 30 while in an inflated state. In at least some embodiments, the convex surface has a profile of a spherical cap formed by a sphere cut off by a plane other than at the center of the sphere. In this manner, the profile of a spherical cap is contrasted to a simple hemisphere, in that the plane does not pass through the center of the sphere. Further, the radius of the sphere from which the spherical cap is taken is larger than the radius of body 202 where body 202 is substantially cylindrical. Other geometries are contemplated to increase surface area and provide reduced inflection points that would otherwise inflict trauma to an environment.

According to embodiments, and as shown in FIGS. 4C and 4D, inter alia, flanges 206 define interruptions 208 around at least a portion of a perimeter of head 204. Interruptions 208 may be configured to further distribute forces applied at head 204. For example, where head 204 is of a flexible material, interruptions 208 allow flanges 206 to flex more easily to conform somewhat under load and reduce pressure points.

Flanges 206 defining interruptions 208 may be configured to facilitate securement, attachment, or interfacing with a securement device, such as a snare. For example, a snare configured to secure by radial constriction may better secure to flanged tip 200 by way of at least one interruption 208. Further, interruptions 208 eliminate a need to constrict a securement device on body 202, entirely below head 204. Rather, interruptions 208 provide locations for securement when a securement device only partially surrounds flanged tip 200. Attachment within interruptions 208 may be made more secure where flanges 206 are of a rigid or semi-rigid material.

According to embodiments, rounded tip 100 and flanged tip 200 are shown in FIG. 5. As shown in FIG. 5, flanged tip 200 may be disposed at an end of intragastric device 10. Head 204 of flanged tip 200 may extend a distance away from balloon 30 such that recess 220 is defined between flanges 206 and balloon 30. Recess 220 may provide a location for securement to intragastric device 10.

The lower profile and atraumatic design does not pose any new risks to the placement procedure, and the lower profile and larger surface area of the distal surface make it more atraumatic than the rounded tip when in situ and inflated, partially inflated or deflated.

According to embodiments, halo tip 300 may be provided to selectably seal the distal end of intragastric device 10. According to embodiments, as shown in FIGS. 6A, 6B, 6C, 6D, 6E, and 6F, halo tip 300 may be provided for an end of intragastric device 10. Halo tip 300 may be coupled to an end of intragastric device 10 at shaft 20. For example, plugs 310 of halo tip 300 may be aligned relative to lumens 40 of shaft 20, whereby plugs 310 seal lumens 40 at ends thereof. Further, guidewire hole 312 of halo tip 300 may be aligned relative to guidewire channel 12 of shaft 20.

At least a portion of each plug 310 is configured to seal at least a portion of a corresponding lumen 40 when halo tip 300 is coupled to shaft 20. Accordingly, plugs 310 may be of a rigid, semi-rigid, or flexible material to facilitate such sealing. The geometry of the plugs 310 may correspond to that of the lumens 40. For example, plugs 310 may have similar cross-sectional geometry as that of the lumens 40, to provide proper sealing. The size, diameter, etc. of plugs 310 may exceed that of lumens 40 by a margin sufficient to facilitate sealing against pressure from within lumens 40. For example, radial pressure provided outwardly from plug 310 against walls of lumen 40 into which it is inserted may provide frictional forces, electrostatic forces, Van der Waals forces, or hydrogen bonding forces, inter alia, to resist pressure from within lumen 40 tending to push plug 310 out of lumen 40.

According to embodiments, and as shown in FIGS. 6A, 6B, 6C, 6D, 6E, and 6F, halo tip 300 includes body 302 and ring 304. Body 302 and ring 304 may be connected by bridge 330. Bridge 330 may be of a rigid, semi-rigid, or flexible material to facilitate such a connection. Where bridge 330 is rigid, the orientation and position of ring 304 relative to body 302 is fixed. Where bridge 330 is flexible, the orientation and position of ring 304 relative to body 302 is at least somewhat variable. Single of multiple bridges 330 may be provided. According to embodiments, ring 304 is within a plane orthogonal to an axis of shaft 20.

According to embodiments, ring 304 may be solid or have a hollow center. Where ring 304 has a hollow center, a guidewire may freely pass there through as emerging from guidewire hole 312.

According to embodiments, and as shown in FIGS. 6B, 6E, and 6F, ring 304 and body 302 define recess 320 there between and adjacent to bridge 330. Recess 320 may expose interior portions of halo tip 300 and provide a securement location for devices to act upon halo tip 300. For example, recess 320 may facilitate operation of a snare or other device on halo tip 300, as disclosed further herein.

According to embodiments, rounded tip 100 and halo tip 300 are shown in FIG. 7. As shown in FIG. 7, halo tip 300 may be disposed at an end of intragastric device 10. Ring 304 of halo tip 300 may extend a distance away from balloon 30 such that recess 320 is defined between ring 304 and balloon 30. Recess 320 may provide a location for securement to intragastric device 10. As shown in FIG. 7, halo tip 300 may provide a curved, rounded, convex, or otherwise low profile contour.

Ring 304 may be configured to facilitate securement, attachment, or interfacing with a securement device, such as a snare. For example, a snare configured to secure by radial constriction may better secure to halo tip 300 by way of recess 320. According to embodiments, retrieval devices 400 (e.g., loop snare, forceps, etc) may secure around bridge 330 or around a section of ring 304 (i.e., through a hollow center of ring 304), as shown in FIG. 8.

According to embodiments, at least one leash 500 may be provided outside balloons 30 for access and securing by a retrieval device, as shown in FIG. 9.

According to embodiments, leashes 500 accommodate the use of forceps for explanting in single or multiple locations. Leashes 500 are of any shape that facilitates securing to a retrieval device, such as hoops, rings, hooks, articulated joints, curved portions, clasps, fasteners, pins, clips, flanges, straps, combinations thereof, etc. According to embodiments, leashes 500 may be rigid, semi-rigid, flexible, or combinations thereof. Leashes 500 may be of materials that are acid resistant and otherwise resilient to a gastric environment. Leashes 500 may be disposed near at least one of a proximal end, a medial portion, and a distal end of intragastric device 10. Leashes 500 may be secured relative to a component of intragastric device 10, such as shaft 20.

According to embodiments, leashes 500 may be flexible or pliable to provide atraumatic functionality. For example, leashes 500 may be configured to conform against a portion of intragastric device 10 during implant and deployment of the gastric device, so as not to impede travel of the gastric device via the esophagus, inter alia. Leashes 500 may be configured to extend away from the gastric device at the time of explant to facilitate retrieval. For example, leashes may extend in a natural state, and retract or compress under light loads. As used herein, "natural state" means a state in which a component is not subject to significant external forces.

According to embodiments, at least one leash 500 may be provided within a balloon 30 for access and securing by a retrieval device, as shown in FIG. 10. According to embodiments, leashes 500 are disposed within balloon 30 of intragastric device 10, such that leashes 500 does not protrude outside intragastric device 10 while balloon 30 is inflated and intact. Leashes 500 within balloon 30 may be accessible upon entry into balloon 30, for example, after deflation thereof by puncture during an explant procedure.

According to embodiments, leashes 500 accommodate the use of forceps for explanting in multiple locations. Leashes 500 are placed inside balloon 30. After deflation and tearing/venting of balloon 30, leashes 500 will be exposed and accessible for removal. Leashes 500 keep the balloon profile unchanged relative to a device without leashes. Leashes 500 further provide an atraumatic in situ outer profile or footprint.

Where more than leash 500 is provided, a variety of retrieval options are provided, wherein a retrieval device may secure to any one or more of the plurality of leashes 500. The options for different securing locations provides the ability to implant, explant, transfer, or otherwise manipulate the gastric device in ways that provide customizable solutions to address a variety of needs. An option for multiple retrieval locations decreases explant procedure time because of the ease of access as shown in FIGS. 9 and 10. Leashes 500 can also be positioned/placed in locations that cannot be accessed with more rigid explants features (i.e. monofilament line that is more flexible than high durometer silicone).

According to embodiments, intragastric device 10 comprises one or more balloons 30 and shaft 20 extending there through. According to embodiments, shaft 20 may be of a material having one or more of a variety of hardnesses. For example, shaft 20 may be of a material having hardness between about 55 A and about 80 A durometer.

According to embodiments, intragastric device 10 having a softer shaft (between about 50 A durometer and about 60 A durometer) demonstrated improved trackability through anatomical challenges such as curves and turns during device placement and explants. The softer shaft (about 55 A) translates about one third of the cantilever force of the stiffer shaft (about 80 A). The improved trackability/flexibility of the device is also beneficial in the event that a device extends partially into or completely into the bowels, as the tip will transmit less transverse force when encountering and negotiating tortuosity in the anatomy.

According to embodiments, another benefit of the softer shaft (about 55 A) is that it translates about one third of the column force of the stiffer shaft (about 80 A) under compression. This is a valuable attribute during insertion/placement, in that it may help prevent perforations/ulcers. The reduced force translation also helps during implant life because of reduced axial force applied to the stomach through the center of the shaft (helps prevent ulcers), whether the balloon or balloons are fully inflated, partially inflated or completely deflated.

According to embodiments, the softer shaft is also easier to explant. The main user interface benefit of the softer shaft is the ability to bend in the center—essentially folding the device along a midsection—with less force (smaller profile) than a stiffer shaft (larger profile). This provides a user with additional options for explant without injuring the patient.

The stiffer shaft requires greater force to kink/fold as evidenced by the cantilever & compression force being approximately 3 times higher for the stiff shaft as compared to the soft shaft. The clinical impact is that when grabbed in a location causing it to fold when pulled through the esophagus, the soft shaft will generate one third of the force of the stiff shaft, making it easier to remove and less likely to cause trauma or dislodge from the removal device during explant.

The devices and methods have been discussed with respect to gastric devices, inter alia. It should be understood that components and methods disclosed herein are applicable to a variety of implantable medical devices, such as any medical device that is implanted in the body of a patient and that may be retrieved at a later time.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An implantable gastric device, comprising:
a shaft having a distal end and a proximal end;
a balloon coupled to the shaft;
a flanged tip disposed at one of the distal end or the proximal end of the shaft and positioned at an outer surface of the balloon, the flanged tip comprising a body connected to the shaft and a head attached to the body and spaced apart from the shaft, wherein—
    the head includes a plurality of flanges extending radially outward from the body,
the flanges define a plurality of interruptions around at least a portion of a perimeter of the head, and
    the flanges form an interrupted and atraumatic surface facing away from the balloon at an end of the flanged tip.

2. The implantable gastric device of claim 1,
wherein the shaft further comprises a lumen extending axially within the shaft from the proximal end to the distal end and fluidly connected to an interior of the balloon; and
wherein the flanged tip further comprises a plug configured to seal the lumen at the distal end when the flanged tip is coupled to the shaft.

3. The implantable gastric device of claim 1,
wherein the shaft further comprises a guidewire channel extending axially within the shaft from the proximal end to the distal end; and
wherein the flanged tip further comprises a guidewire hole configured to be aligned with the guidewire channel of the shaft when the flanged tip is coupled to the shaft.

4. The implantable gastric device of claim 1, wherein a recess is defined between the flanges, the body, and the balloon, wherein the recess provides a location for securing a retrieval device.

5. The implantable gastric device of claim 1, wherein provides a substantially smooth, convex surface.

6. The implantable gastric device of claim 5, wherein the convex surface is shaped such that imaginary extensions of the convex surface extending from the flanges as viewed in profile are aligned to tangentially graze the surface of the balloon while in an inflated state.

7. The implantable gastric device of claim 5, wherein the convex surface has a profile of a spherical cap formed by a sphere cut off by a plane other than at the center of the sphere.

8. The implantable gastric device of claim 7, wherein the body is substantially cylindrical.

9. The implantable gastric device of claim 8, wherein the radius of the spherical cap is larger than the radius of the body.

* * * * *